US00PP18253P3

(12) United States Plant Patent
Eggleton

(10) Patent No.: US PP18,253 P3
(45) Date of Patent: Nov. 27, 2007

(54) *VIOLA* PLANT NAMED 'LORD PRIMROSE'

(50) Latin Name: *Viola×hybrida.*
Varietal Denomination: Lord Primrose

(76) Inventor: Steven Eggleton, 3 Harris Road, Wonga Park, Melbourne, Vic (AU), 3115

( * ) Notice: Subject to any disclaimer, the term of this patent is extended or adjusted under 35 U.S.C. 154(b) by 22 days.

(21) Appl. No.: 11/435,488

(22) Filed: May 16, 2006

(65) Prior Publication Data

US 2006/0282926 P1 Dec. 14, 2006

(30) Foreign Application Priority Data

Jun. 9, 2005 (AU) ..... 2005/175

(51) Int. Cl.
*A01H 5/00* (2006.01)

(52) U.S. Cl. ..... Plt./323

(58) Field of Classification Search ..... Plt./323
See application file for complete search history.

(56) References Cited

U.S. PATENT DOCUMENTS

2006/0282926 P1 * 12/2006 Eggleton ..... Plt./323

OTHER PUBLICATIONS

UPOV ROM GTITM Computer Database 2006/04 Citation for 'LORD Primrose'.*

* cited by examiner

*Primary Examiner*—Wendy C. Haas

(57) ABSTRACT

A new cultivar of *Viola* plant named 'LORD PRIMROSE' characterized by dense trailing habit, dome shape, green leaves and fragrant flowers that are violet and mid-yellow in color. In combination these traits set 'LORD PRIMROSE' apart from all other existing varieties of *Voila* known to the inventor.

2 Drawing Sheets

Genus: Viola Species: ×*hybrida.*
Denomination: 'LORD PRIMROSE'.

BACKGROUND OF THE INVENTION

The present invention relates to a new and distinct variety of viola grown as an ornamental plant for use in containers, woodland gardens, landscape borders, and as a bedding plant. The new cultivar is known botanically as *Viola*× *hybrida* and will be referred to hereinafter by the cultivar name 'LORD PRIMROSE'.

'LORD PRIMROSE' was selected by the inventor in a cultivated area of Victoria, Australia, as an individual hybrid that resulted from the deliberate cross-pollination of *Viola* 'Major Primrose' (unpatented) and *Viola* 'Etain' (unpatented). The breeding program began in July 2001 with the goal of producing new viola plants that exhibit unique habit and flower colors. The seed parent is *Viola* 'Major Primrose' and the pollen parent is *Viola* 'Etain'. The seed that resulted from this deliberate cross-pollination was germinated, and the resulting seedlings grown to flowering maturity in 140 mm containers. From these flowering plants, the inventor selected 'LORD PRIMROSE' for its combination of compact plant habit, domed plants shape, and flower color.

The new *Viola* variety named 'LORD PRIMROSE' exhibits dense compact habit, domed plant shape, medium-green leaves with rounded teeth, and violet flowers with mid-yellow centers. 'LORD PRIMROSE' is distinguishable from the seed parent by the color of the central flower petal. The central flower petal of 'Major Primrose' is light yellow to white in color. 'LORD PRIMROSE' is distinguishable from the pollen parent by the central flower petal. 'Etain' exhibits no dominant central flower petal color. 'LORD PRIMROSE' exhibits a dominant central flower petal that is mid-yellow and violet in color. The closest comparison plant is 'Major Primrose'. 'LORD PRIMROSE' is distinguishable from the comparison plant by the mid-yellow and violet central flower petal.

The first asexual propagation was conducted by the inventor in March 2002 in a cultivated area of Victoria, Australia. The method of asexual propagation utilized was stem cuttings. Since that time 'LORD PRIMROSE' has been determined stable and reproduces true to type in successive generations of asexual propagation.

SUMMARY OF THE INVENTION

The following traits have been repeatedly observed and represent the distinguishing characteristics of the new plant cultivar 'LORD PRIMROSE'. In combination these traits set 'LORD PRIMROSE' apart from all other *Viola* known to the inventor. 'LORD PRIMROSE' has not been tested under all possible conditions and phenotypic differences may be observed with variations in environmental, climatic and cultural conditions, without however, any variance in genotype.

1. 'LORD PRIMROSE' exhibits dense compact habit.
2. 'LORD PRIMROSE' is dome-shaped.
3. 'LORD PRIMROSE' blooms from spring to fall.
4. 'LORD PRIMROSE' exhibits a central dominant flower petal.
5. 'LORD PRIMROSE' exhibits fragrant flowers that are violet and mid-yellow in color.
6. 'LORD PRIMROSE' exhibits medium-green leaves with rounded teeth.

7. 'LORD PRIMROSE' is asexually propagated using stem cuttings.
8. 'LORD PRIMROSE' is 20 cm in height and 40 cm in width at maturity.
9. 'LORD PRIMROSE' is hardy to USDA Zone 7.
10. 'LORD PRIMROSE' is grown for use in containers, woodland gardens, landscape borders, and as a bedding plant.

BRIEF DESCRIPTION OF THE DRAWINGS

The accompanying color drawings illustrate the overall appearance of the new *Viola* cultivar named 'LORD PRIMROSE' showing the colors as true as it is reasonably possible to obtain in colored reproductions of this type. Colors in the drawings may differ from the color values cited in the detailed botanical description, which accurately describe the actual colors of the new *Viola* variety named 'LORD PRIMROSE'.

The drawing labeled

The drawing labeled

Figure 1:
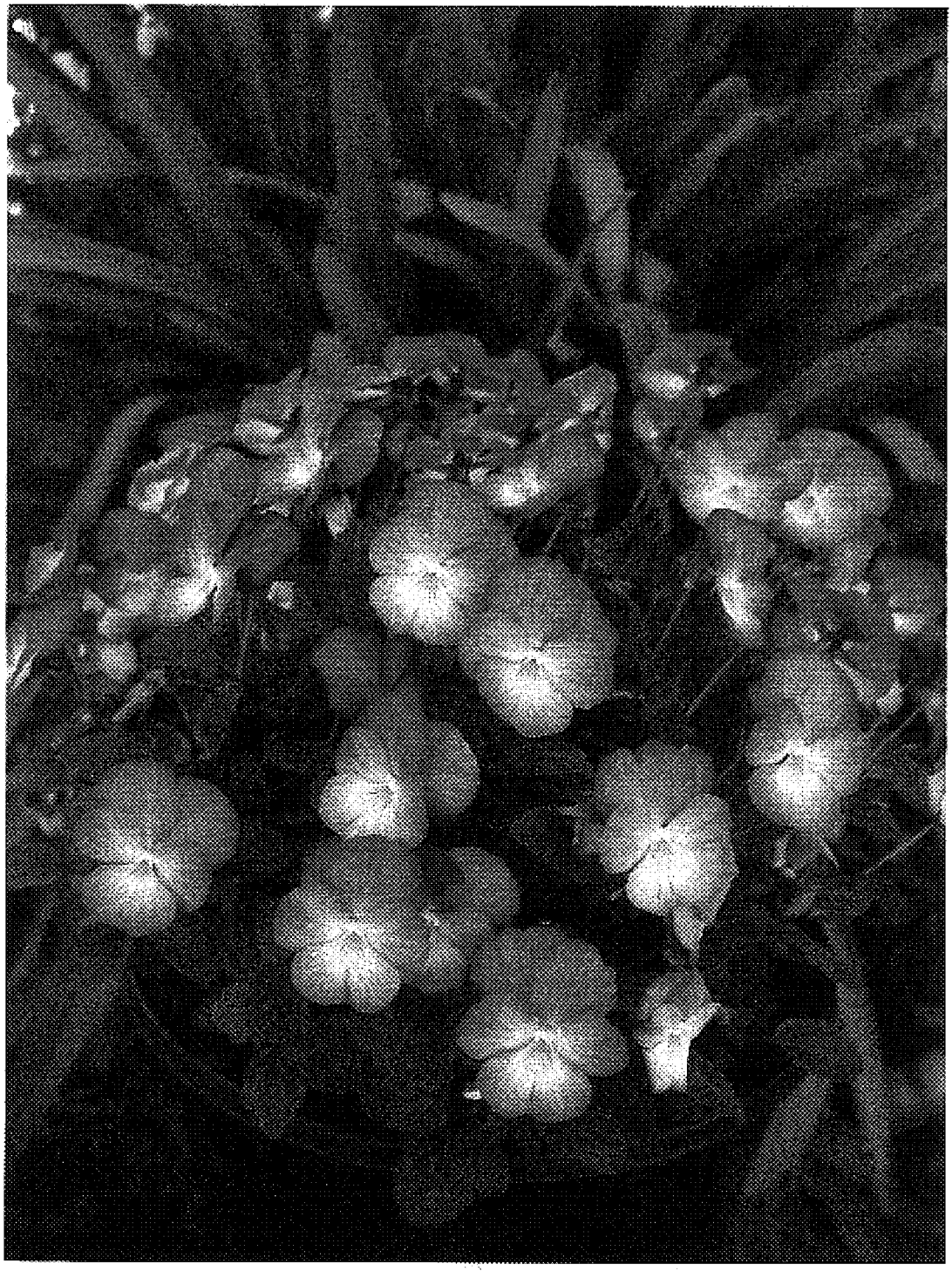
FIG. 1 depicts a whole plant from a side perspective.
Figure 2:
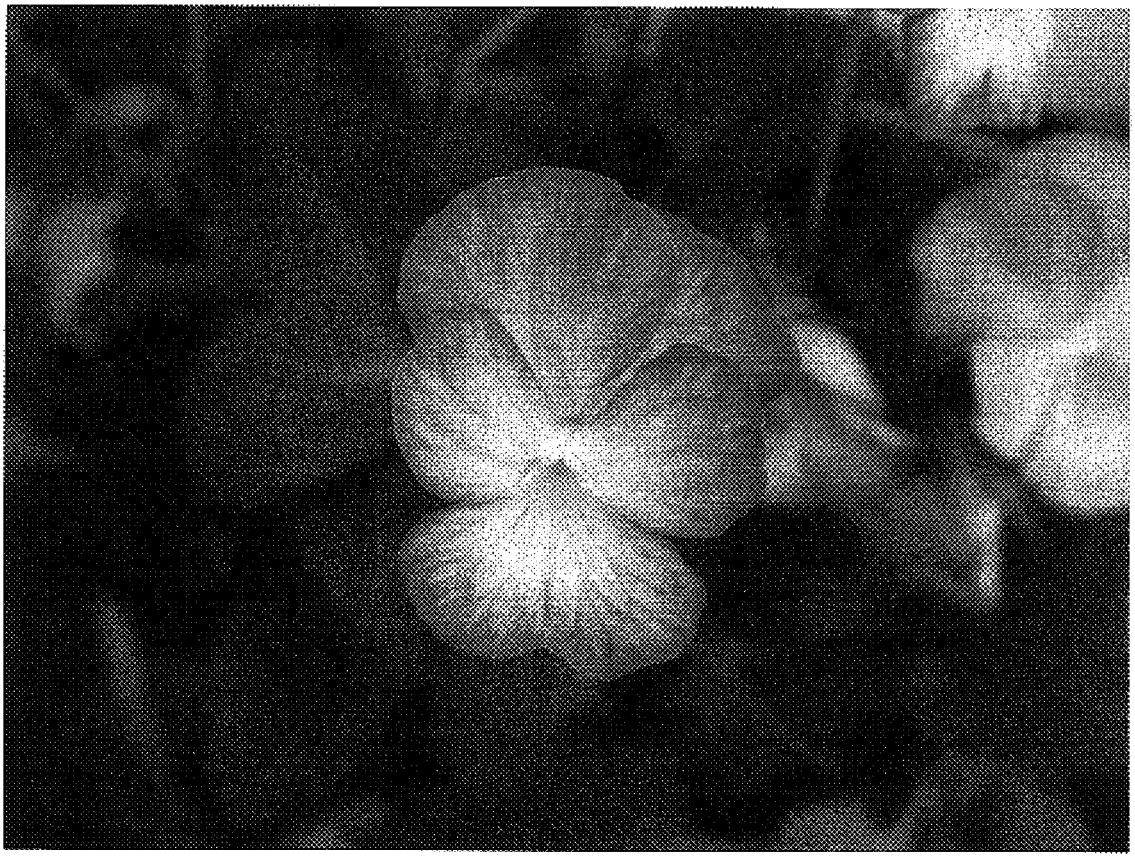
FIG. 2 depicts a close-up view of the flower.

Drawings were made using conventional techniques and although colors may appear difference from actual colors due to light reflectance they are as accurate as possible by conventional photography.

BOTANICAL DESCRIPTION OF THE PLANT

The following is a detailed description of the new *Viola* plant named 'LORD PRIMROSE'. Data was collected in Arroyo Grande, Calif. from 12-month-old plants growing in 2-liter containers. Phenotypic differences may be observed with variations in environmental, climatic, and cultural conditions without however, any variance in genotype. The color determinations are in accordance with the 2001 Royal Horticultural Society Colour Chart of London, England, except where general color terms of ordinary dictionary significance are used. The growing requirements are similar to that of other *Viola*.

Botanical classification; *Viola×hybrida* 'LORD PRIMROSE'.
Plant genus: *Viola*.
Plant species: *×hybrida*.
Plant denomination: 'LORD PRIMROSE'.
Common name: *Viola*.
Plant type: Perennial herb.
Plant use: Grown for use in containers, woodland gardens, landscape borders, and as a bedding plant.
Cultural requirements: Plants in full sun or partial shade using well-drained moderately fertile soil, and moderate water.
Pests and disease susceptibility: No pests or disease are known to the inventor other than those commonly affecting *Viola*.
Parentage: *Viola×hybrida* 'LORD PRIMROSE' is a hybrid plant that resulted from the deliberate cross-pollination of the following parent plants:
*Seed parent.*—*Viola* 'Major Primrose'.
*Pollen parent.*—*Viola* 'Etain.'
Plant description:
*Bloom period.*—Spring to fall.
*Plant habit.*—Dense compact habit.
*Plant shape.*—Dome-shaped.
*Plant height* (*at maturity*).—20 cm in height.
*Plant width* (*at maturity*).—40 cm in width.
*Plant hardiness.*—USDA Zone 7.
*Asexual propagation.*—Asexual propagation is accomplished using the method of stem cuttings.
*Time to develop roots.*—4–6 weeks are needed for initial cuttings to develop roots.
*Crop time.*—6 months are needed to produce a finished 1-liter container from a rooted cutting.
Stem:
*Branching pattern.*—Densely branching.
*Stem shape.*—Trigonous.
*Stem color.*—144B.
*Stem texture.*—Flexible.
*Stem width.*—An average of 3 mm in width.
*Stem length.*—An average of 5 cm in length.
*Stem surface.*—Glabrous.
*Internode length.*—A range of 2 cm to 4 cm in length.
Foliage:
*Length arrangement.*—Alternate.
*Leaf shape.*—Ovate.
*Leaf division.*—Simple.
*Leaf apex.*—Obtuse.
*Leaf base.*—Rounded.
*Venation pattern.*—Pinnate.
*Vein color* (*adaxial and abaxial surfaces*).—147B.
*Leaf margin.*—Crenate.
*Leaf surface* (*adaxial and abaxial surfaces*).—Glabrous.
*Leaf appearance.*—Matte.
*Leaf length.*—1.25 cm to 4.50 cm.
*Leaf width.*—1 cm to 1.25 cm.
*Leaf color* (*adaxial surfaces*).—147A.
*Leaf color* (*abaxial surfaces*).147B.
*Leaf attachment.*—Petiolate.
*Petiole color.*—144A.
*Petiole shape.*—Sulcate.
*Petiole surface.*—Glabrous.
*Petiole length.*—An average of 4.50 cm.
*Petiole width.*—An average of 2 mm.
*Stipules.*—Present.
*Stipule arrangement.*—Opposite.
*Stipule form.*—Leaf-like.
*Stipule attachment.*—Sessile.
*Stipule shape.*—Lyrate.
*Stipule color* (*adaxial and abaxial surfaces*).—138A.
*Stipule margin.*—Cleft.
*Stipule apex.*—Rounded.
*Stipule base.*—Truncate.
*Stipule surface* (*adaxial and abaxial surfaces*).—Glabrous.
*Stipule length.*—An average of 2.25 cm.
*Stipule width.*—An average of 1.50 cm.
*Leaf fragrance.*—Grass-like.
Flowers:
*Inflorescence type.*—Solitary.
*Flower shape.*—Orbicular.
*Flower aspect.*—Pendant.
*Flower persistent or self-cleaning.*—Self-cleaning.
*Flower length.*—3.25 cm.
*Flower width.*—2.75 cm.
*Flower depth.*—1.10 cm.
*Flower color.*—Individual colors 86C, 86D, 13A, 13D are present on an individual flower.
*Bud dimensions.*—0.50 cm in length and 0.50 cm in width.

*Bud shape.*—Globular.
*Bud color.*—86A.
*Bud surface.*—Puberulent.
*Bud apex.*—Obtuse.
*Petals.*—5 in number.
*Petal shape.*—Obdeltoid, obcordate, and obovate petal shapes are individually present on an individual flower.
*Petal color* (*adaxial surface*).—Colors 86C, 13D, and 13A are individually present on an individual petal.
*Petal color* (*abaxial surface*).—Colors 86D and 13D are individually present on an individual petal.
*Petal surface* (*adaxial and abaxial surfaces*)—Glabrous.
*Petal dimensions.*—Individual petals have been observed with the following dimensions: 1 cm in length, 1.25 cm and 1.5 cm in width; 1.25 cm in length, 1.25 cm, 1.5 cm and 2.0 cm in width.
*Petals fused or unfused.*—Unfused.
*Petal margin.*—Entire.
*Petal apex.*—Obcordate and obtuse apices are individually present on the petals of an individual flower.
*Petal base.*—Cuneate.
*Spur.*—One in number on anterior petal of an individual flower.
*Spur color.*—189B.
*Spur surface.*—Glabrous.
*Spur length.*—1 cm. in length.
*Spur width.*—2.75 mm in width.
*Corolla tube depth.*—6 mm in depth.
*Calyx diameter.*—2.25 cm in diameter.
*Calyx shape.*—Stellate.
*Sepals.*—5 in number.
*Sepal shape.*—Lanceolate.
*Sepal length.*—1 cm in length.
*Sepal width.*—3 mm in width.
*Sepal color* (*abaxial surface*).—138B.
*Sepal color* (*adaxial surface*).—138A.
*Sepal apex.*—Acute.
*Sepal base.*—Rounded.
*Sepal margin.*—Entire.
*Sepal surface* (*abaxial and adaxial surfaces*).—Glabrous.
*Peduncle length.*—Ranges from 4.5 cm to 11 cm in length.
*Peduncle width.*—2 mm in width.
*Peduncle shape.*—Sulcate.
*Peduncle color.*—144A.
*Peduncle surface.*—Glabrous.
*Flower fragrance.*—Perfume scent.
*Lastingness of flower.*—An individual flower lasts 5–7 days.

Reproductive organs:
*Stamens.*—5 in number.
*Stamens shape.*—Pandurate.
*Stamen arrangement.*—Introrse and enclosing ovary.
*Stamen color.*—160D.
*Stamen dimensions.*—3 mm in length and 2 mm in width.
*Anther color.*—N167A.
*Anther dimensions.*—1 mm in length and 1.25 mm in width.
*Anther form.*—Crisped.
*Pollen quantity.*—Moderate.
*Color of pollen.*—155A.
*Pistil.*—1 in number.
*Pistil dimensions.*—7.50 mm in length.
*Pistil color.*—144D.
*Style shape.*—Cylindrical.
*Style length.*—2 mm in length.
*Style color.*—144D.
*Stigma shape.*—Globular.
*Stigma color.*—144B.
*Stigma dimensions.*—1.50 mm in height and 1.50 mm in width.
*Ovary position.*—Superior.
*Ovary color.*—144B.
*Ovary shape.*—Ovoid.
*Ovary dimensions.*—4 mm. in height and 3 mm. in diameter.

Seed production: No seed observed to date.

What is claimed is:

1. A new and distinct cultivar of *Viola* plant named 'LORD PRIMROSE' as described and illustrated herein.

* * * * *